United States Patent [19]

Cansell et al.

[11] Patent Number: 5,569,808
[45] Date of Patent: Oct. 29, 1996

[54] METHOD FOR REGULATING A PROCESS FOR THE SEPARATION OF ISOMERS OF AROMATIC HYDROCARBONS HAVING FROM 8 TO 10 CARBON ATOMS

[75] Inventors: François Cansell, Montreuil; Gérard Hotier, Rueil Malmaison; Philippe Marteau, Paris; Nathalie Zanier, Rueil Malmaison, all of France

[73] Assignee: Institut Francais Du Petrole, Rueil-Malmaison, France

[21] Appl. No.: 268,174

[22] Filed: Jun. 29, 1994

[51] Int. Cl.$^6$ ................................... C07C 7/00
[52] U.S. Cl. ................ 585/800; 585/812; 422/82.05; 422/82.09; 356/301
[58] Field of Search .................... 585/800, 812; 422/82.05, 82.09; 356/301

[56] References Cited

FOREIGN PATENT DOCUMENTS

92/16274  10/1992  WIPO ................ B01D 15/02

OTHER PUBLICATIONS

Roberts et al., "Development and Application of a Raman Spectroscopy, . . ." 8131 Advances in Instrumentation and Control 45(1990) Part 1, pp. 463–468.
Garrison et al., "Raman Spectroscopy for On-Line Distillation Process Control", 8131 Advances in Instru. & Control, 44(1989) Part 1, pp. 357–363.
Angel et al., "Simultaneous Multi-point Fiber-optic Raman Sampling . . . " SPIE vol. 1587 Checm., Biochem. & Environ. Fiber Sensors III(1991)219–231.
Wei, Chiu–Nan, "Diagnose Process Problems", Chemical Engineering Progress Sep. 1991, 70–74.
Balannec et al., "From Batch Elution to Simulated Countercurrent Chromatography", Preparative and Production Scale Chromatography, pp. 301–357. No Date.

*Primary Examiner*—Asok Pal
*Assistant Examiner*—In Suk Bullock
*Attorney, Agent, or Firm*—Millen, White, Zelano & Branigan, P.C.

[57] ABSTRACT

A monochromatic light signal of a wavelength of between 400 and 1300 nanometers is simultaneously passed by a source 1, a beam splitter 2 and optical fibers 3, 3a to at least two points of a zone 9 for the separation of a mixture of isomers and aromatic hydrocarbons having from 8 to 10 carbons atoms. A polychromatic signal is recovered corresponding to the Raman effect between 400 and 3500 cm$^{-1}$ by optical receiving fibers 5, 5a connected to sensors 4 at the locations of said points. The chemical composition of the mixture is determined from the Raman spectra obtained by a spectrometer 6. The analysis sequence is repeated, the profiles with respect to the concentration of the isomers in the mixture are reconstituted and by comparison with reference concentration profiles, action is taken on at least on operational variable 11, 12 of the separation process. Application of this process to the regulation of simulated mobile beds, a distillation operation or a crystallization process for obtaining paraxylene or orthoxylene are also provided.

11 Claims, 7 Drawing Sheets

METHOD FOR REGULATING A PROCESS FOR THE SEPARATION OF ISOMERS OF AROMATIC HYDROCARBONS HAVING FROM 8 TO 10 CARBON ATOMS

FIELD OF THE INVENTION

The invention concerns a method and an apparatus for regulating a process for the separation of isomers of aromatic hydrocarbons having from 8 to 10 carbon atoms.

BACKGROUND OF THE INVENTION

The separation of paraxylene from the aromatic $C_8$ cut is conventionally effected either by one of the crystallisation processes or by the procedure involving adsorption in a simulated mobile bed (see the prior art of French patent No 91/11004). The separation of orthoxylene is conventionally effected by superfractionating.

For those processes the aim to be achieved is the production of an isomer with a given level of purity in a manner which remains constant with the passage of time.

An excessively low level of purity can very seriously reduce its commercial value to such a degree as to make it impossible to sell while an excessively high level of purity gives rise to an increase in operating costs.

Hitherto it was possible to achieve that check on purity in two ways:

1) Measurements of flow rates and analysis operations at points in the flows passing into and issuing from the unit in such a way as to establish detailed balance sheets with respect to the materials involved. Then, by comparison with model material balance sheets and correlating the influence of each of the operational variables, possibly modifying one or more operational variables in order to stay within the desired range of values in regard to yield and purity. The frequency with which that kind of balance sheet is established is from one to several times per day. That means that in order to guarantee a predetermined level of purity in spite of the minor random fluctuations in the operational variables, it is necessary to aim at a level of purity which is slightly greater, which has an adverse effect on operating costs.

2) In-line analysis of the effluents by means of vapour phase chromatography. That method makes it possible to react quickly in the face of a drop in purity which suddenly occurs. For the product which is outside the specification may be recycled in order not to pollute the storage tank which is in the course of being filled. In addition, measurement of the operational variables and parameters will make it possible to rapidly modify the appropriate setting or settings. Such modification may be effected either by means of empirical correlations or by means of software for dynamic simulation of the unit which is based on predictive modelling of the unit. The article 'Diagnosis process problems' in chem. Eng. Prog. V87, No 9, pages 70–74 (1991) summarizes the most advanced state of the art.

As regards more precise analysis of the level of purity of p-xylene, it can be measured by gaseous phase chromatography or by measurement of the crystallisation point. The method involving measurement of the crystallisation point only works with relatively rich mixtures (at least 8%) of paraxylene, and it is therefore not universal, even for paraxylene. It was also analysed by near infrared spectroscopy (Ed Stark et col. SPIE Vol 1575, pages 70–86, 1991). The optical fibers which can be used in near infrared have higher coefficients of attenuation than the used in the visible range and do not allow the use of very substantial transmission distances.

The frequency of analysis by means of vapour phase chromatography is such that it is however only possible to carry out a few measurements per hour and the result is produced only some ten minutes after the sampling operation.

In the case of recrystallisation however, provided that the composition of the charge to be treated is indeed constant, precise temperature measurements at different points in the process permit excellent regulation of the degree of purity of the paraxylene produced.

Unfortunately, in the case of chromatography in a simulated mobile bed, simply measuring a parameter such as temperature does not make it possible to establish a purity regulation chain.

In the case of distillation (production of orthoxylene by superfractionating) simply measuring temperature is not sufficiently precise since the total temperature difference or variation is from 5° to 7° Celsius for 300 real plates. We are therefore proposing measurement in real time simultaneously at a plurality of points which are internal to the separation process of the composition of the mixtures in a fluid phase, with a measurement apparatus which is disposed away from the separation unit. The analysis method selected is Raman spectroscopy.

The literature is very abundant as regards the potentialities of Raman spectroscopy for in-line real-time and multipoint analysis of solutions in an industrial environment. S M Angel et col, (SPIE Vol 1435, Optical methods for ultra sensitive detection and analysis, Techniques and Applications (1991)) describe a system made up of a laser diode, an FT-Raman spectrometer and a CCD detector (Charge Coupled Diode). The fiber length is 4 m. In order to attenuate the Raman spectrum of the collecting fiber, two emitting and collecting fiber configurations are proposed. The ends of the fibers are disposed at 360° or 180° from each other, The solutions analysed are pure solutions of naphthalene and toluene. No quantitative analysis is effected. The same authors in SPIE Vol 1587, Chemical, Biochemical and Environmental Fiber Sensor III (1991), use the sees assembly for simultaneous analysis at four points with four laser diodes. The emitting and collecting fibers are positioned in facing relationship or form an angle of 15°. The acquisition times vary between 1 and 30 seconds. The assembly is used for monitoring a column for distillation. In the case of water/ethanol separation by distillation, the percentage of ethanol is determined after calibration. A potential application related to distillation of petroleum cuts is discussed with quantification of the percentage of toluene and benzene with acquisition times of 60 seconds.

M J Roberts et col. in Process Control and Quality, 1 (1991), 281–291, Elsevier Science Publishers B. V. Amsterdam, describe the limitations of Raman spectroscopy for in-line real-time and multipoint analysis, for the purposes of chemical analysis. Different factors such as the type of components, their number, their concentration, the number of analysis points, the level of precision and the response time are discussed. In order to be free of the Raman spectrum of the collecting fiber, calculations are made to determine the angle between the collecting fibers and the emitting fibers, taking account of the refractive indices of the medium and attenuation of the fibers in relation to the wavelength of use. The Raman spectrum of cyclohexane is present with 35 m of optical fibers of silica, positioned at an angle of 10°.

The same authors, in ISA, 1990, 0065-2814/90/pages 463–468, apply the following assembly to the operation of a water-isopropanol distillation column: the source is formed by a Ya g-Nd laser, while a mechanical multiplexer makes it possible alternatively to select one of the six emitting fibers. The emitting and receiving fibers are made up of fibers of 400 μm in diameter, of doped silica-silica. The optical sensor in the true sense is formed by the assembly in a stainless steel tube terminated by a sapphire window of 1) in a central position, the emitting fiber, and 2) at a peripheral position, 4 to 6 collecting fibers. The measurement cell is formed by a cylindrical cell of a minimum dimension of 90 mm by 50 mm in diameter, equipped with a flowmeter and a thermocouple. The spectrometer is equipped with a filtering system permitting elimination of the Rayleigh diffusion signal, for each spectrum, the acquisition time is 2.2 minutes and the degree of precision of chemical analysis is 3% on mixtures in the range of 5%–95% to 95%–5%.

M A Leugers et al in SPIE, Vol 1990, Chemical, Biochemical and Environmental Applications of Fibers (1988), developed a probe formed by a collecting fiber at the centre and six receiving fibers around it. The probe is used for quantitative analysis of benzene/toluene mixtures. When applied in the petroleum field, Raman spectrometry is used (U.S. Pat. No 5,139,334) for the measurement of properties such as the octane number, the percentage of aromatics and mono/di-aromatics distribution. U.S. Pat. No 2,527,121 discusses determining the amount of total aromatics in mixtures of hydrocarbons by Raman spectrometry.

It is found therefore on the one hand that analysis of the aromatic cut $C_8$ when pure or diluted by a solvent (mixtures of 4 or 5 constituents in any proportions) has never been effected with that type of assembly, and on the other hand quantification of mixtures, even binary mixtures, is still fairly imprecise and generally does not cover the whole range of composition. On the other hand, in the prior-art assemblies, the authors have recourse either to a plurality of laser sources or to mechanical multiplexing: these are example and expensive constructions. Concerning the use of a plurality of sources, when these are laser diodes, the spectral width is generally fairly substantial and it does not make it possible to obtain spectra which are appropriate for furnishing precise quantification of the mixtures having four or five constituents. When lasers are involved, besides the considerable increase in costs that this entails, it is difficult to provide that all sources emit precisely on the same wavelength, which is revealed by virtue of the fact that each of the spectra obtained is slightly displaced with respect to the others and that it is not possible to use a single quantification software. In addition, the optical sensors and the measuring cells proposed are also expensive end sophisticated. Finally, in the situation where optical fibers have been used, they never exceed a length of 50 m, which makes it entirely possible for the laser source and the spectrometry to be moved away to a control room or a laboratory. However moving the laser source and the spectrometer away in that fashion is absolutely essential since it is illusory to try to place sophisticated and non-deflagrationproof optical instruments directly within an industrial separation unit.

SUMMARY OF THE INVENTION

One of the objects of the invention is to remedy the disadvantages of the prior art.

Another object is to determine the profiles in respect of concentration of at least two isomers contained in a mixtures isomers in the course of separation in at least one separation zone.

Another object involves a method of regulating a process for the separation of at least one isomer of aromatic hydrocarbon having from 8 to 10 carbon atoms in a mixture comprising at least two of said isomers.

Another object concerns a method of regulating a process for the separation of paraxylene in a mixture of aromatic $C_8$ hydrocarbons which is more or less dilute in a solvent such as toluene or paradiethylbenzene.

Generally the invention concerns a method of regulating a process for the separation of at least one isomer of aromatic hydrocarbon having from 8 to 10 carbon atoms which is contained in a mixture comprising at least two of said isomers, said process comprising a separation step under appropriate conditions in a separation zone, said method being characterized in that:

a) a monochromatic light signal of a wavelength of between 400 and 1300 nanometres and preferably between 420 and 650 nanometres is simultaneously sent to at least two suitable points of said zone, other than points at which effluents are taken off, b) a diffused polychromatic signal is recovered corresponding to the Raman effect between 400 and 3500 $cm^{-1}$, substantially at the level of said points of said separation zone of a), and preferably between 600 and 1200 $cm^{-1}$, c) the two signals recovered are simultaneously sent to a multi-channel spectrometer delivering the corresponding Raman spectra, d) the chemical composition it ion of the mixture at each of the two points is determined from the two spectra, e) the sequence of a, b, c and d is repeated so as to reconstitute the profiles in respect of concentration of the two isomers contained in the mixture, and f) the profiles in respect of concentration obtained are compared to reference concentration profiles and adjustment is made of at least one operational variable of the separation process for regulating the process.

The frequency of the analysis operations may be up to one measurement per second and the delay between measurement and result can be less than 100 milliseconds. Therefore, for each measurement point, there is obtained a curve in respect of composition in dependence on time, which is virtually continuous, with an extremely short response delay.

The regulating method according to the invention may be applied to a process for adsorption in a simulated mobile bed, in co-flow or in counter-flow mode, while the isomer in the para position can be collected either in a fraction referred to as the extract or in a fraction referred to as the raffinate. In that case, from the concentration profiles obtained, it is possible to adjust at least one of the following operational variables to regulate the process:

the flow rate of solvent, the flow rate of charge the flow rate of extract and therefore raffinate the internal reflux flow rate of the isomer being sought, and the internal flow rates of each of the zones of the adsorption procedure.

It can also be applied to a process for the crystallization of a mixture in at least one crystallisation zone comprising paraxylene and in which the chemical composition of the mixture is determined at at least two distinct points in said zone. In that case, on the basis of the concentration profiles obtained, it is possible to adjust at least one of the following operational variables to regulate the process:

temperature the rewashing rate, and the speed of agitation.

It can also be used in the distillation of that mixture of compounds, in respect of which the chemical composition is determined at at least two and preferably four points in the distillation unit. In that case, on the basis of the concentration profiles obtained, it is possible to adjust at least one of the following operational variables to regulate the process:

the charge flow rate the reflux rate the flow rate of distillate the amount of heat supplied to the reboiler.

A feature of the invention comprises usually determining the chemical composition of the mixture in liquid phase or in vapour phase and at temperatures of between −70° C. and +220° C.

In accordance with another feature of the invention the monochromatic emission signal can also be passed on to at least one of the effluents from the separation process in question, and in that case its chemical composition is determined in accordance with the method of the invention, the composition of the effluent is compared to a reference composition, and action is possibly taken on the operational variables of the process. Monitoring the composition of the effluent in that way avoids polluting a storage tank with a product which is suddenly degraded. The present method can be applied to the separation of a mixture comprising paraxylene, orthoxylene, metaxylene and ethylbenzene in the presence of a solvent such as toluene or paradiethylbenzene. It can also be applied to the separation of a mixture comprising aromatic $C_9$ and/or $C_{10}$ isomers.

The invention also concerns the apparatus for carrying the method into effect.

More precisely the apparatus comprises in combination:

a laser or laser diode source of monochromatic light signals which emits in the visible range or in the near infrared and which is connected to a beam splitter, at least two optical emission fibers and preferably at lest four optical fibers connected to the beam splitter, at least two sensors and preferably at least four sensors connected to the optical emission fibers and disposed on the inside or the outside of the separation enclosure, each of the two sensors being disposed at a suitable point on the enclosure such that the sample of mixture analysed is of substantially homogeneous liquid, at least two optical collecting fibers near preferably at least four connected to the sensors, at least one multi-channel Raman spectrometer connected to the optical collecting fibers and adapted to produce Raman spectra which are representative of the mixture, and means for processing the spectra which are connected to the spectrometer and adapted continuously to determine the chemical composition of the mixture and the profiles in respect of concentration of the mixture.

Thus, by virtue of the light beam splitter coupled to a single source of monochromatic light signals, it is possible to provide for emission strictly on the same wavelength at different internal points in the separation enclosure, thereby to produce Raman spectra in which the width of lines is cell small that it permits quantitative measurements.

In accordance with a feature of the apparatus it may comprise means for regulating an operational variable (for example a flow control valve), which are controlled by the processing means. More precisely the processing means are generally connected to a computer which compares the results obtained to previously recorded concentratin profiles and which, by acting for example on at least one flow regulating valve as referred to above, corrects the drifts or variations in concentration profiles recorded continuously.

In accordance with an alternative form of the apparatus the separation enclosure may comprise at least two optical casings in which the mixture circulates and which are dispose at the location of the measurement points and which each comprise a porthole, preferably of sapphire, facing towards the sensors, each of the sensors being disposed at a distance of at most 500 mn from the portholes and advantageously between 50 and 200 nm.

In accordance with another alternative form of the apparatus the separation enclosure my comprise at least two casings in which the mixture circulates and which are disposed at the location of the measurement points, each of the casings being penetrated by an optical emitting fiber and a collecting fiber, said fibers being disposed in the casing at a suitable angle which is calculated in dependence on the refractive index of the mixture and the numerical aperture of the fibers.

Having regard to the requirements in regard to safety on industrial sites, those optical fibers may be of a length which can attain 1000 m, for example between 40 and 1000 m.

Good results have been obtained with fibers from 50 to 400 m in length.

The invention will be better appreciated from the following drawings diagrammatically illustrating the process end the apparatus, in which.

Figure 1:
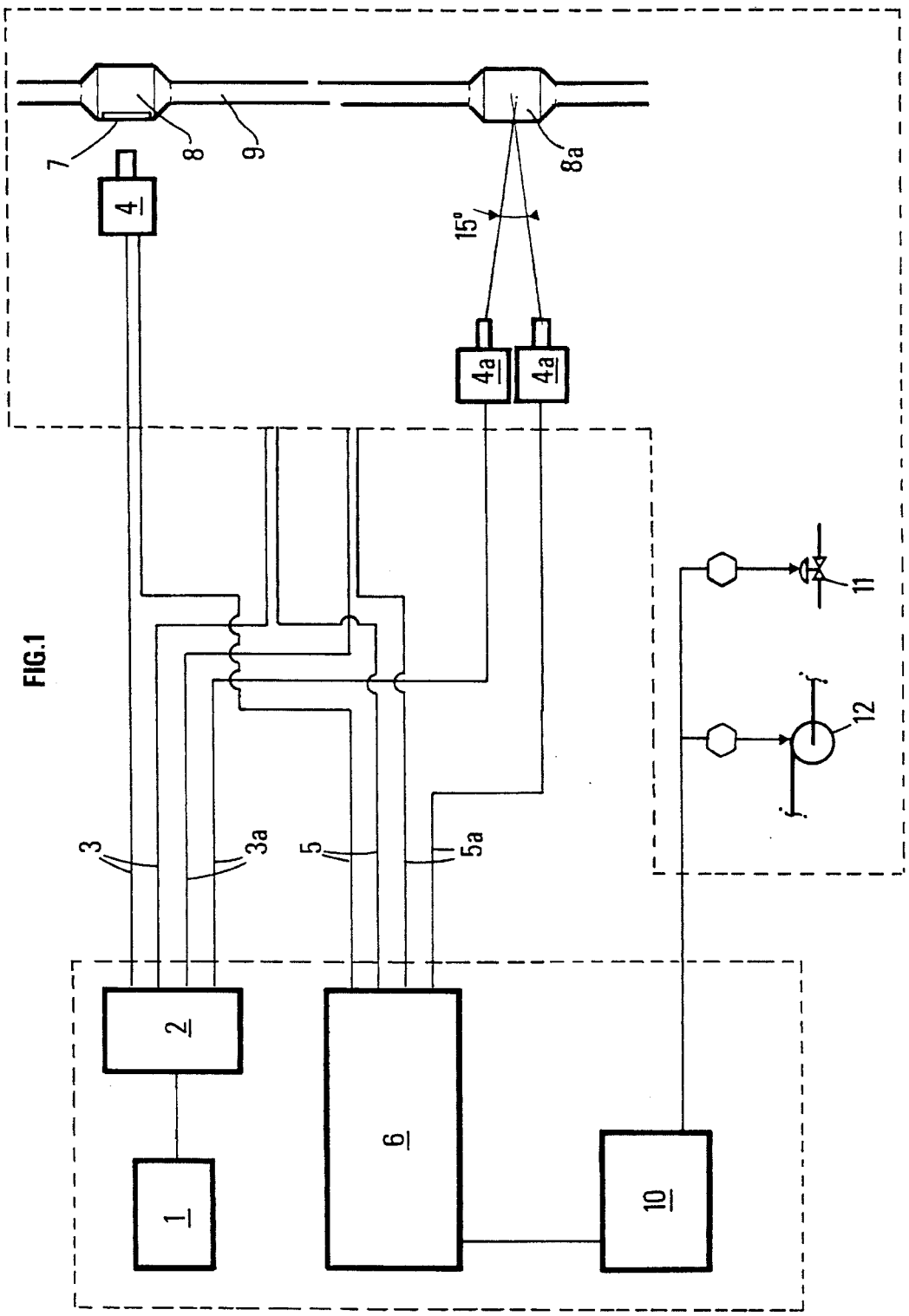
FIG. 1 shows the apparatus.

The apparatus which is diagrammatically shown in FIG. 1 is divided over two locations, one where there are a laser source 1 and a Raman spectrometer 6, and the other being an apparatus 9 for the separation of aromatic $C_8$ isomers (for example a simulated counterflow mobile bed), on which sensors 4 are disposed. Those two locations are connected by eight fibers 3, 5: four fibers 3 transport the exciting light of the laser to the sensors 4 while the other four fibers 5 return the diffused signal of the sensors to the spectrometer 6.

On issuing from the laser the beam is focussed on the entry fiber of a commercially available bean splitter 2 (ref. SEDI coupler 1–4) which simultaneously sends a monochromatic excitation signal to a representative sample in the adsorption column 9. An alternative to that assembly (not shown in the Figure) involves sending the beam to an optical multiplexer (network or cascade of separating devices) and focussing the four beams on each of the four fibers 3.

The optical fibers used for the assembly are of silica with a core of 100 μm, and a total diameter of 125 μm (numerical aperture 0.22). The sensors 4 are of two types depending on whether the temperature is lower than or higher than 80° C. Below 80° C. the sensor 'Super Dilor Head' operates in a back-scattering mode on the outside of a porthole 7 of an optical casing 8 which is mounted on the adsorption column 9 and in which the mixture circulates. The fibers are directly connected to the sensor. It will be appreciated that it is possible to thermally insulate the 'Super Dilor Head' in such a way that its temperature remains below 80° C. while the analysed mixture flowing behind the porthole is at a higher temperature. Above 80° C., in another embodiment, the emitting fiber 3a and the collecting fiber 5a which are connected to the sensor 4a penetrate into the optical casing 8a at an angle of 15' relative to each other and are placed directly in the mixture. Sealing integrity is ensured by stuffing boxes (not shown in the Figure). It should be noted that a special fiber has to be used for high temperatures (up to 280° C.). The 'Super Dilor Head' is a known device which is intended to prevent any exciting light from pass jag into the return fibre and generating therein the Raman spectrum of silica. The intrusive system has the same characteristic, at least in regard to the molecules involved in the processes for the separation of the aromatic $C_8$ molecules, but it is less luminous. It nonetheless withstands high temperatures, unlike the 'Super Dilor Head'.

The optical casings are of the same type and are mounted on a conduit of the unit by suitable connections. For the 'Super Dilor Head' they are provided with a porthole of sapphire. In the situation where the two fibers pass into the optical casing the sapphires are replaced by a plate in which the stuffing boxes for the fibers are mounted. All the fiber connections are of standard type (SNA 905), including the connections to the spectrometer.

Eight fibres can be connected to the input of the Raman spectrometer 6. A stigmatic system 10 makes it possible simultaneously to obtain the eight corresponding spectra in displaced relationship on a CCD (Charge Coupled Diode) detector (2-dimensional multi-channel), and, by repeating the same sequence of steps, to obtain a profile in respect of the concentrations of the constituents of the mixture within the separation column by mane of a suitable computer. The data processing means moreover make it, possible to control a valve for controlling the flow rate of the extract for example, as indicated at 11, or a pump for controlling the flow rate of solvent, for example, as indicated at 12.

Figure 2:
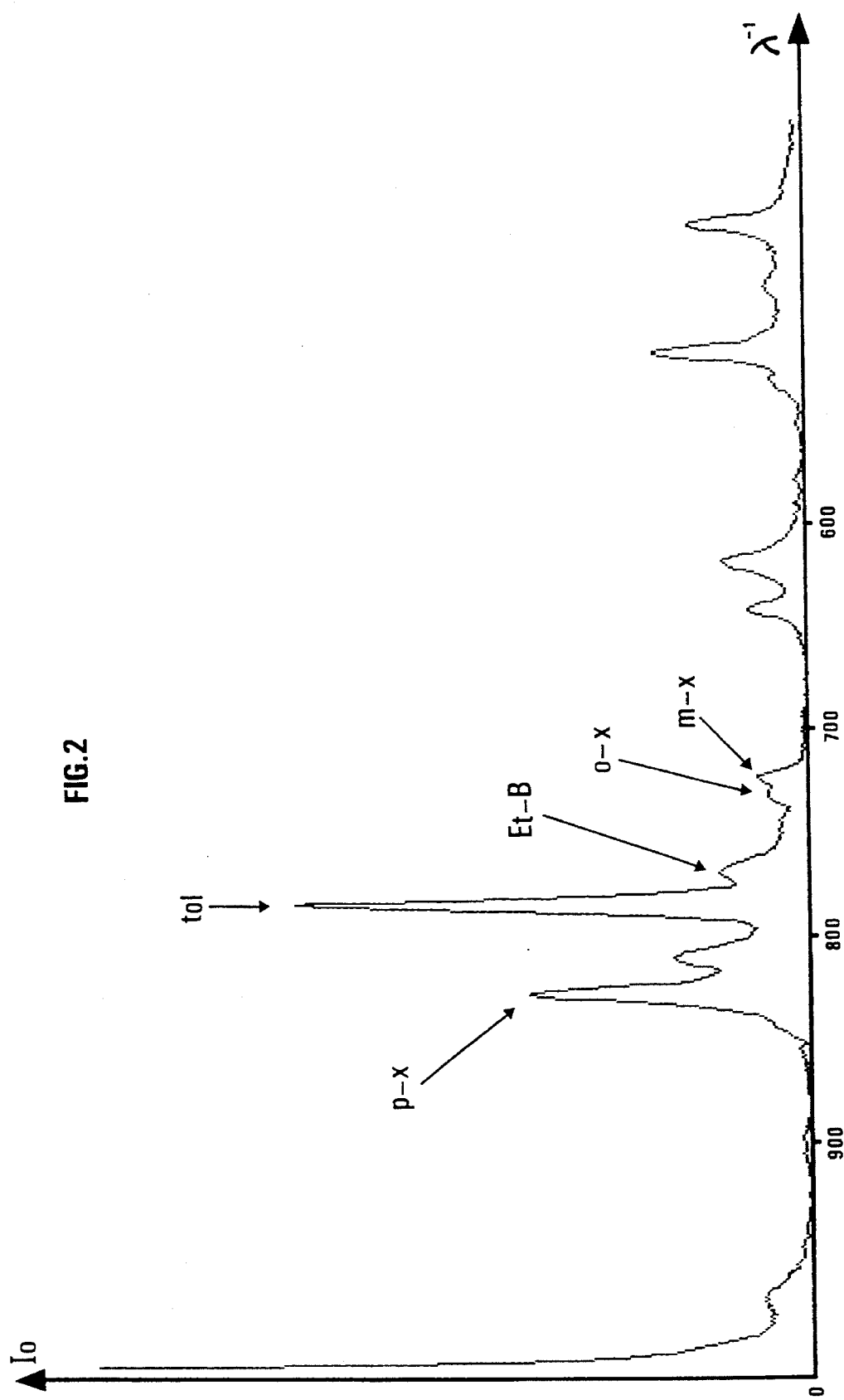
FIG. 2 shows the optical intensity of the Raman signal from a mixture of aromatic isomers having 8 carbon atoms in dependence on the number of waves.

The Raman spectra of the molecules encountered in the paraxylene separation processes have more or less intense lines over a very wide spectral range (0–3,500 cm$^{-1}$). It is however necessary to find a range which is sufficiently reduced for it to be seen at the same time by the detector and in which the is a line that is at least sufficiently fine and intense per constituent to be analysed, the preferred range being from 675 to 915 cm$^{-1}$. The spectrum illustrated in FIG. 2 shows in fact that the ends of that range, which are free of any emission, make it possible to determine the base line and that each molecule has a line there.

Calculation in respect of the concentrations involved is effected by measuring the heights of the peaks. Matrix calculation makes it possible to take account of overlaps. Let Ij be the intensity of a line due to the molecule j and let Mj be the measured intensity. That gives:

$$Mj = \sum_j Cij \cdot Ij. \tag{1}$$

The coefficients Cij are determined on the basis of the spectra of the pure products. Let [k] be the matrix of the coefficients Cij, let [I] be that of Ij and let [M] be that of Mj. That will give:

$$[I] = [k^{-1}] \cdot [M] \tag{2}$$

The intensities I j which are standardised by the relative effective diffusion sections are then proportional to the relative densities of the molecules. The values J are obtained by the spectra of equimolar binary mixtures. Finally, the concentration of the molecule j is given by:

$$C_j = \frac{Ij/\Omega j}{\sum_j Ij/\Omega j}. \tag{3}$$

It is to be noted that the operation of determining the values $\Omega j$ also involves matrix calculation in order to take account of possible overlaps. In addition the values Cj and the values $\Omega j$ must be known in dependence on temperature.

Although it is preferable to effect calculation in respect of the levels of concentration by the method of heights, in the case of a substantial enlargement of the lines (for example at high temperature), it is possible to have recourse to the method of surface areas, it being known that each line is represented by a Lorentz curve and that in the event of interference it will be necessary to carry out calculations for deconvolution of those curves.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications cited herein are hereby incorporated by reference.

EXAMPLE NO. 1

Table I sets out the results of the measurements effected on various mixtures of the five constituent para, meta, ortho-xylenes, ethylbenzene and toluene. Shown therein are the real concentrations 1) and those measured by Raman spectrometry 2) and 3), on the tank 2) which is connected directly to the macro input of the spectrometer and after a displacement of 200 m by means of optical fibers 3). A spectrum example is shown in FIG. 2 where the optical intensity of the Raman signal of the mixture 5 is plotted in dependence on the wave number, the acquisition time being 10 seconds. Table II shows in fact the precision obtained in dependence on the number of measurements accumulated: it can be seen that a duration of 10 seconds is sufficient.

In these two Tables the wavelength used was 514.5 nm obtained with a 1.3 W power ionised argon laser. Those spectra are acquired on a Raman spectrometer, Dilor model XY.

The calculation software packages are installed on a PC model 486.

EXAMPLE NO. 2

This Example uses a simulated mobile bed pilot separation unit composed of 24 columns of a length of 1 m end a diameter of 1 cm, filled with a KBa exchanged zeolite Y. Between each two columns, it is possible to introduce charge or solvent or else to take off an extract or a raffinate by means of four assemblies equivalent to four 24 plus one way valves. This installation has already been described in French patent No 91/11004 and in the book: Preparative and production scale chromatography, G Barker and G Ganestos, Marcel Dekkar Inc Editions New York, September 1992, pages 301–349.

In comparison with the description of those two references, four cells have been added, in which liquid runs out and at which there terminate a 200 m source optical fiber connected to the source laser of Example 1 and a 200 m receiving optical fiber connected to the spectrometer with matrix of receivers 2 D in Example 1. They are respectively disposed between the columns 4 and 5, the columns 12 and 13, and the columns 20 and 21, and between the multi-position extract valve and the extract draw-off pump.

The elution solvent selected is toluene.

The composition of the charge is as follows: toluene 2.276%, ethylbenzene 11.120%, paraxylene 22.453%, metaxylene 49.708%, orthoxylene 14.351%. The whole of the apparatus is raised to 150° C.

The permutation period selected is 100 seconds and the whole of the cycle therefore lasts for 40 minutes. The respective reference flow rates are as follows (expressed at 150° C.):

Solvent: 8.635 cm³/min
Extract: 8.44 cm³/min
Zone 1: 42.395 cm³/min
Zone 2: 33.955 cm³/min
Charge: 5.415 cm³/min
Raffinate: 5.61 cm³/min
Zone 3: 39.37 cm³/min
Zone 4: 33.76 cm³/min while the measured flow rates are as follows:

Solvent ; 8.61 cm³/min, that is to say 10.545 g/period
Extract : 8.40 cm³/min, that is to say 10.287 g/period
Charge : 5.445 cm³/min, that is to say 6.669 g/period
Raffinate : 5.59 cm³/min, that is to say 6.856 g/period
Losses : 0.065 cm₃/min, that is to say 0.071 g/period (i.e. 0.46%).

TABLE 1

Concentrations of the 8 mixtures: 1) announced 2) measured in tank and 3) with 125 μm fibre. In the last case the mixtures are at 200 m from the spectrometer and the exciter laser.

| Mixture | Concentration | Toluene | m-Xylene | p-Xylene | o-Xylene | Ethyl-Benz. |
|---|---|---|---|---|---|---|
| MIX 1 | 1 announced | 97 | 0 | 3 | 0 | 0 |
|  | 2 in tank | 96.90 | 0.05 | 2.98 | 0.05 | 0.00 |
|  | 3 with fibre | 96.49 | −0.29 | 3.08 | 0.24 | 0.48 |
| MIX 2 | 1 announced | 82 | 0 | 37.85 | 0 | 0.15 |
|  | 2 in tank | 82.34 | 0.06 | 17.64 | −0.05 | 0.01 |
|  | 3 with fibre | 81.85 | −0.06 | 17.92 | 0.17 | 0.11 |
| MIX 3 | 1 announced | 82 | 0.15 | 17.85 | 0 | 0 |
|  | 2 in tank | 81.97 | 0.17 | 17.99 | −0.03 | −0.10 |
|  | 3 with fibre | 81.53 | −0.05 | 18.08 | 0.28 | 0.15 |
| MIX 4 | 1 announced | 82 | 0.10 | 17.70 | 0.05 | 0.15 |
|  | 2 in tank | 82.25 | 0.15 | 17.60 | 0.02 | −0.02 |
|  | 3 with fibre | 81.85 | −0.08 | 17.79 | −0.01 | 0.43 |
| MIX 5 | 1 announced | 50 | 3.5 | 25 | 1.5 | 20 |
|  | 2 in tank | 49.91 | 3.43 | 25.51 | 1.38 | 19.96 |
|  | 3 with fibre | 49.15 | 3.27 | 26.01 | 1.68 | 19.89 |
| MIX 6 | 1 announced | 2 | 50 | 1 | 17 | 30 |
|  | 2 in tank | 1.88 | 49.82 | 0.93 | 17.28 | 30.10 |
|  | 3 with fibre | 2.20 | 48.51 | 1.08 | 17.63 | 30.57 |
| Mix 7 | 1 announced | 30 | 35 | 0.5 | 12.5 | 22 |
|  | 2 in tank | 29.36 | 35.43 | 0.52 | 12.76 | 21.94 |
|  | 3 with fibre | 29.30 | 35.52 | 0.47 | 12.44 | 22.28 |
| MIX 8 | 1 announced | 65 | 20 | 0 | 10 | 5 |
|  | 2 in tank | 65.60 | 19.79 | −0.04 | 9.69 | 4.95 |
|  | 3 with fibre | 64.24 | 19.13 | −0.28 | 9.95 | 4.96 |

TABLE II

Influence of the accumulation time on the level of precision of measurement

| Component | Value announced | 100 accumulations of 1 s | | | | 10 accumulations of 1 s | | | | | 2 accumulations 1 | | |
|---|---|---|---|---|---|---|---|---|---|---|---|---|---|
| | | Sp1 | Sp2 | Sp3 | VM | Sp1 | Sp2 | Sp3 | Sp4 | VM | SP1 | SP2 | VM |
| Toluene | 50.0 | 49.91 | 49.40 | 49.45 | 49.59 | 51.06 | 48.92 | 49.48 | 49.58 | 49.76 | 51.46 | 46.93 | 49.20 |
| m-Xyl | 3.5 | 3.15 | 3.28 | 3.32 | 3.25 | 2.99 | 3.25 | 3.12 | 3.74 | 3.28 | 3.63 | 2.69 | 3.16 |
| p-Xyl | 25.0 | 27.76 | 26.15 | 25.99 | 25.97 | 26.70 | 26.17 | 25.98 | 25.16 | 26 | 26.13 | 28.64 | 27.4 |
| O-Xyl | 1.5 | 1.31 | 1.34 | 1.35 | 1.33 | 1.59 | 1.61 | 1.56 | 1.27 | 1.51 | 1.16 | 1.34 | 1.25 |
| Ethyl-B | 20.0 | 19.87 | 19.83 | 19.89 | 19.86 | 17.65 | 20.06 | 19.86 | 20.25 | 19.46 | 17.62 | 20.40 | 19.01 |

The compositions as measured after 24 hours of steady-state operation of the unit are as follows:

| Extract | Raffinate |
|---|---|
| Toluene: 85.353% | Toluene: 16.168% |
| Ethylbenzene: 0.179% | Ethylbenzene: 10.534% |
| Paraxylene: 14.356% | Paraxylene: 0.270% |

| Extract | Raffinate |
| --- | --- |
| Metaxylene: 0.048% | Metaxylene: 49.041% |
| Orthoxylene: 0.014% | Orthoxylene: 13.987% |

Figure 3:
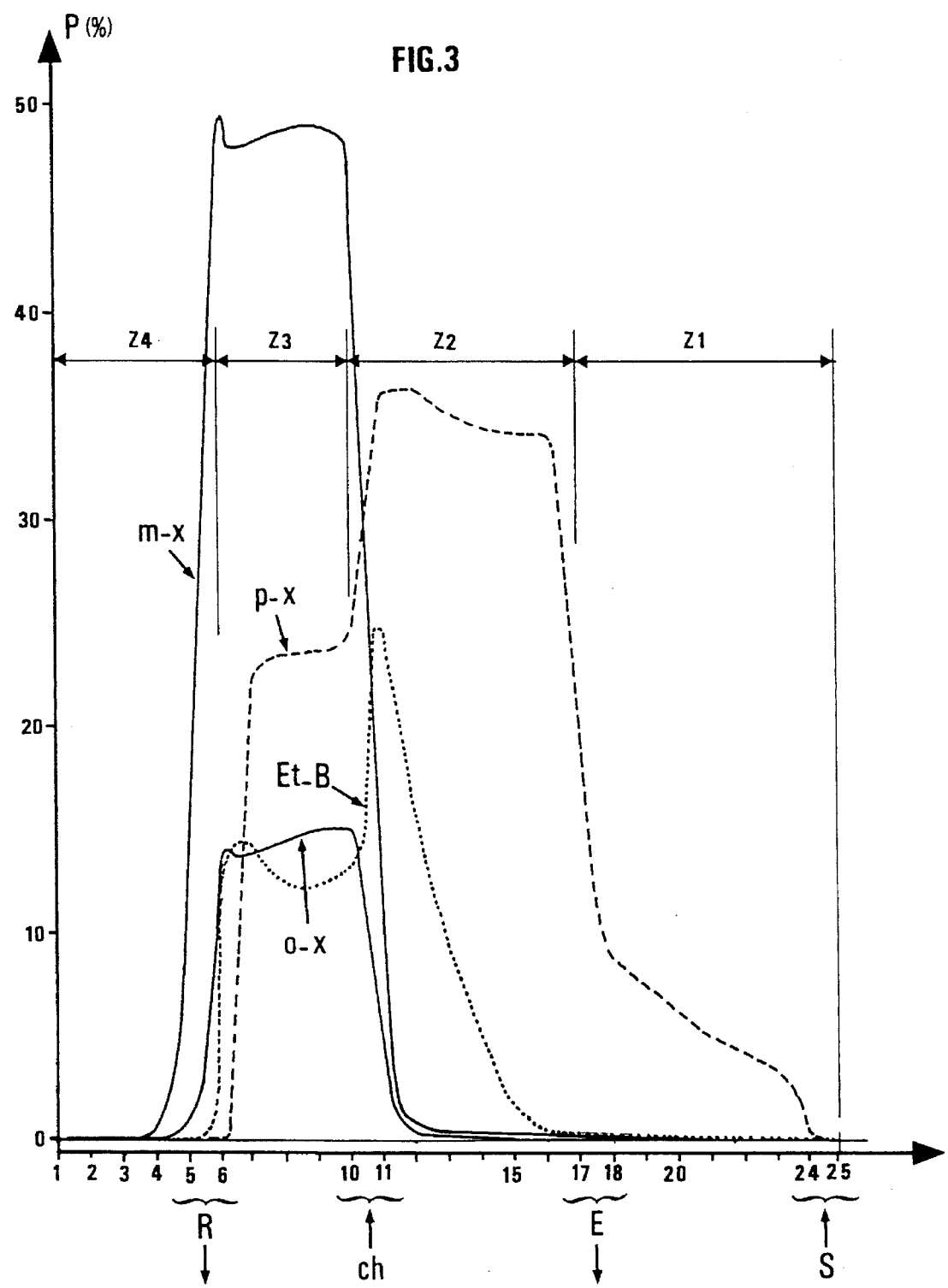
FIGS. 3 to 7 show profiles in respect of concentration of different isomers of a mixture of aromatic hydrocarbons having 8 carbon atoms, for the separation of paraxylene.

By means of the three sensors disposed in the internal circuit, a complete concentration profile is observed every 13 minutes and 30 seconds; such a profile is shown in FIG. 3. It will be noted however by superimposing the profiles given by each of the three sensors that there is a slight displacement corresponding to about 10 seconds. In addition the beginning of the metaxylene peak which occurs at reference 4 indicates an excessively low flow rate in zone 4, which is revealed by an excessively high level of solvent consumption.

EXAMPLE 3

Taking the equipment and the operating conditions as set out above, the unit is put out of order in such a way as to observe the effect of a modification to each of the four recycle flow rates on the concentration profiles.

Procedure No 1: The respective reference flow rates expressed at 150° C. are as follows:

| | |
| --- | --- |
| Solvent: 7.85 cm$^3$/min | Zone 1: 42.395 cm$^3$/min |
| Extract: 8.44 cm$^3$/min | Zone 2: 33.955 cm$^3$/min |
| Charge: 5.415 cm$^3$/min | Zone 3: 39.37 cm$^3$/min |
| Raffinate: 4.825 cm$^3$/min | Zone 4: 34.545 cm$^3$/min |

The losses represent about 0.5% of the total of the inputs. The compositions as measured after 24 hours of operation of the unit are as follows:

| Extract | Raffinate |
| --- | --- |
| Toluene: 85.026% | Toluene: 16.514% |
| Ethylbenzene: 0.217% | Ethylbenzene: 12.042% |
| Paraxylene: 14.303% | Paraxylene: 0.169% |
| Metaxylene: 0.264% | Metaxylene: 55.335% |
| Orthoxylene: 0.090% | Orthoxylene: 15.940%. |

Figure 4:
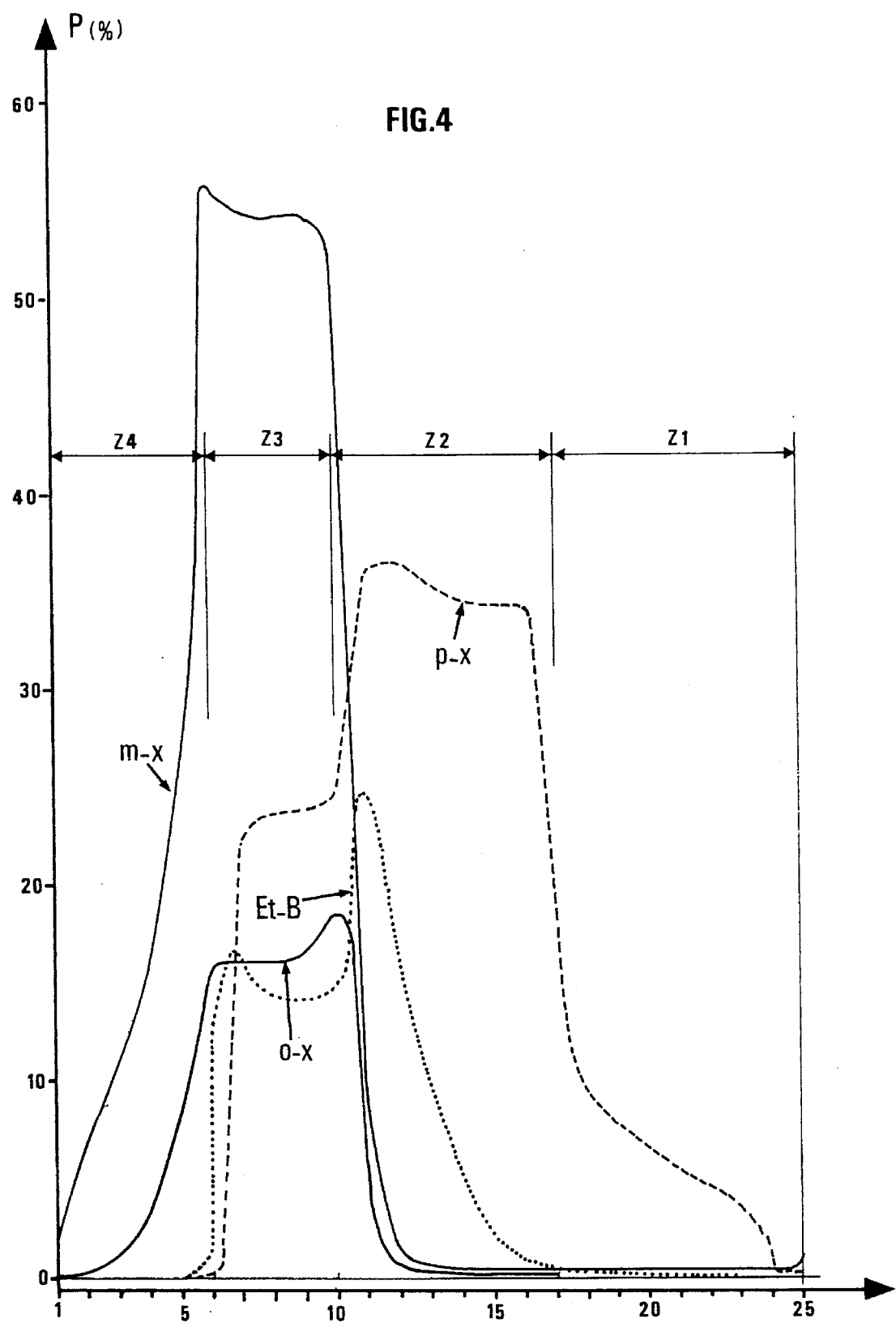

By means of the three sensors disposed in the internal circuit, a complete concentration profile is observed every 13 minutes and 20 seconds. It is noted this time that the start of the metaxylene peak is in fact at reference 1 (FIG. 4). In contrast, unexpectedly, the plateau in respect of metaxylene concentration occurs only at 54.25%. On the other hand, it is necessary to wait for around fifteen cycles in order for a continuous bottom of 0.25% of metaxylene to be established all along the column. When the aim is moderate purity of the extract (95%) for subsequent purification by crystallization as in French patent No 91/11004, that type of concentration profile has to be sought. Simple comparison of the profiles in zone 1 in relation to Examples 2 and 3 (procedure No 2) shows whether the flow rate in that zone does or does not have to be changed.

Procedure No 2: The respective reference flow rates expressed at 150° C. are as follows:

| | |
| --- | --- |
| Solvent: 8.635 cm$^3$/min | Zone 1: 42.395 cm$^3$/min |
| Extract: 8.44 cm$^3$/min | Zone 2: 33.955 cm$^3$/min |
| Charge: 5.995 cm$^3$/min | Zone 3: 39.95 cm$^3$/min |
| Raffinate: 6.19 cm$^3$/min | Zone 4: 33.76 cm$^3$/min. |

The losses represent about 0.5% of the total of the inputs. The compositions as measured after 24 hours of steady-state operation of the unit are as follows:

| Extract | Raffinate |
| --- | --- |
| Toluene: 84.430% | Toluene: 26.777% |
| Ethylbenzene: 0.430% | Ethylbenzene: 10.188% |
| Paraxylene: 15.158% | Paraxylene: 1.083% |
| Metaxylene: 0.046% | Metaxylene: 48.161% |
| Orthoxylene: 0.016% | Orthoxylene: 13.791%. |

Figure 5:
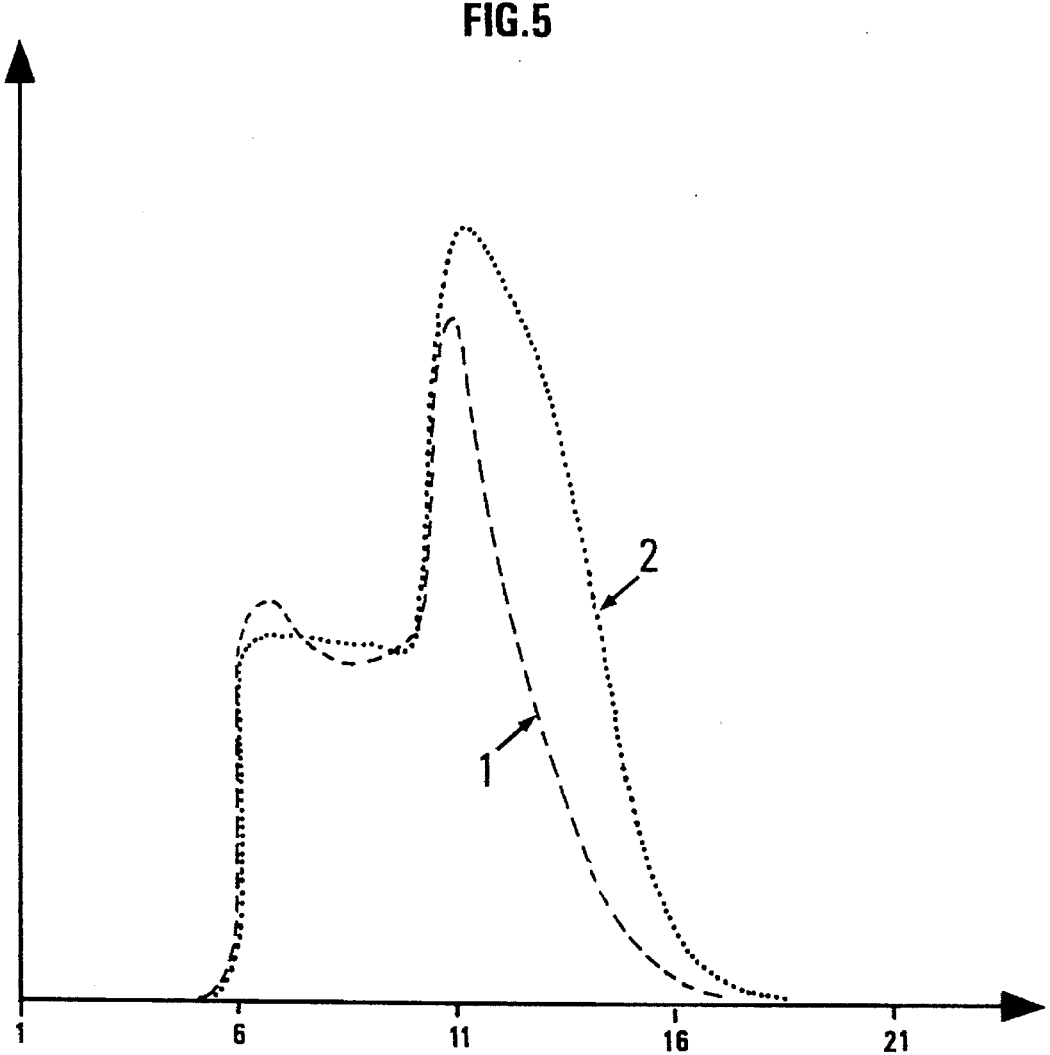

By means of three sensors disposed in the internal circuit, a concentration profile is observed every 13 minutes and 20 seconds. This time, more than forty cycles are required before the ethylbenzene concentration profile stabilizes while a condition of stability is achieved very quickly (about ten cycles) in regard to paraxylene. In relation to procedure No 1, it is noted therefore that the increase in flow rate in zone 3 is not beneficial (drop in yield and purity). On the other hand the deterioration in purity is slow and it is therefore possible to react sufficiently early to an increase in the ethylbenzene inventory in such a way as to avoid pollution of the extract by ethylbenzene, FIG. 5 shows the profiles for ethylbenzene in the case of Example 2 (1) and in the case of procedure No 2 of Example 3 (2), the profiles of the other species being only very slightly modified.

Procedure No 3: The respective reference flow rates expressed at 150° C. are as follows:

| | |
| --- | --- |
| Solvent: 8.635 cm$^3$/min | Zone 1: 42.395 cm$^3$/min |
| Extract: 9.02 cm$^3$/min | Zone 2: 33.375 cm$^3$/min |
| Charge: 5.995 cm$^3$/min | Zone 3: 39.37 cm$^3$/min |
| Raffinate: 5.64 cm$^3$/min | Zone 4: 33.76 cm$^3$/min |

The losses represent about 0.5% of the total of the inputs. The compositions measured after 24 hours of steady-state operation of the unit are as follows:

| Extract | Raffinate |
| --- | --- |
| Toluene: 82.357% | Toluene: 22.385% |
| Ethyl: 2.043% | Ethylbenzene: 8.588% |
| Paraxylene: 14.557% | Paraxylene: 0.578% |
| Metaxylene: 0.048% | Metaxylene: 53.109% |
| Orthoxylene: 0.015% | Orthoxylene: 15.340%. |

Figure 6:
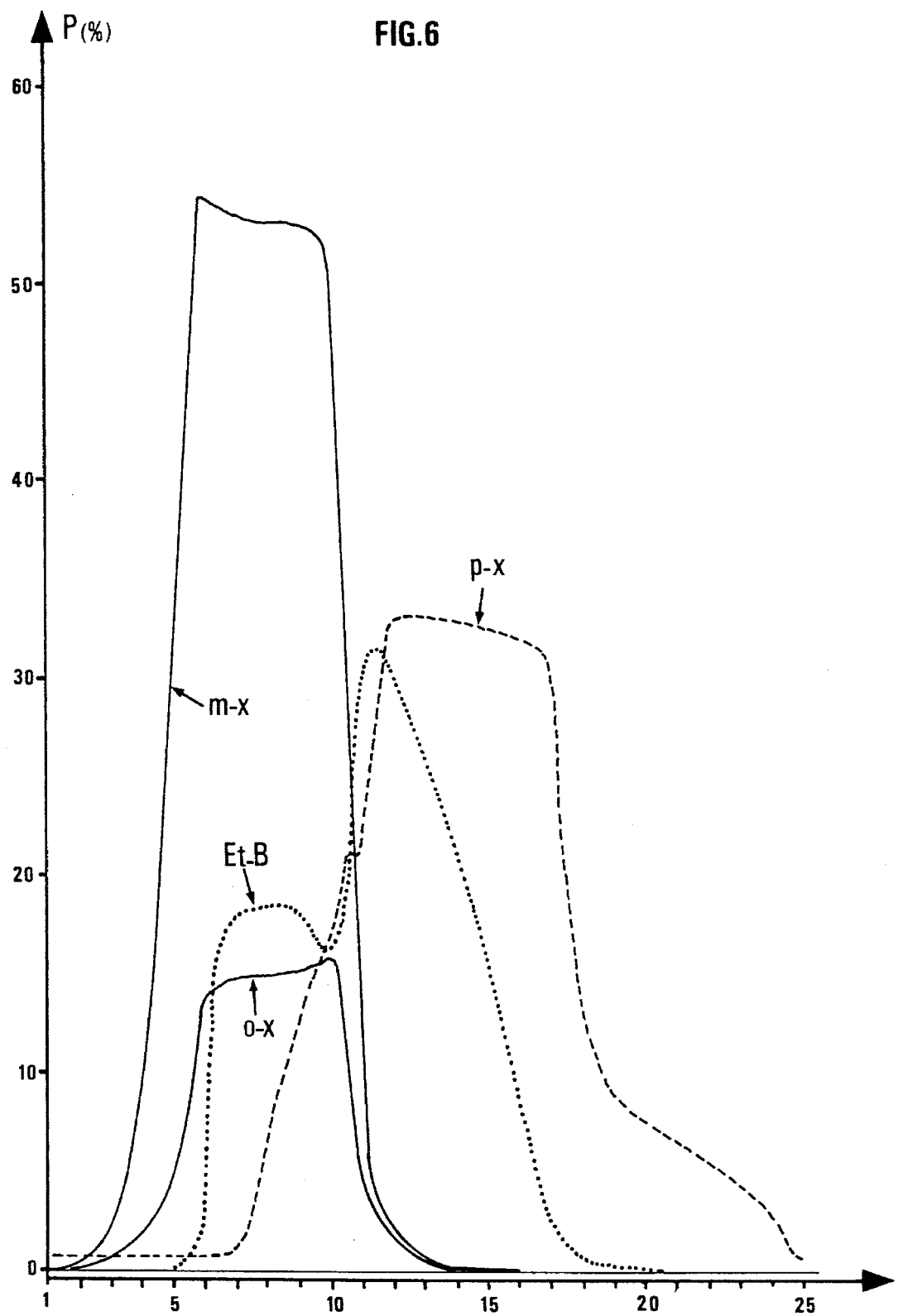

By means of the three sensors disposed in the internal circuit, a concentration profile is observed every 13 minutes and 20 seconds, In relation to procedure No 2 the concentration profiles are amply modified and during the transitional condition the concentration of paraxylene in the extract increases to 18% before stabilising at about 14.5%. For a period of more than forty eight hours the ethylbenzene concentration profile varies and surprisingly the plateau in zone 3 is at a higher level of concentration than in all the other procedures while the level of ethylbenzene in the raffinate constantly falls from 10.2% to 8.6%. Simple visual examination of the concentration profiles in FIG. 6 is sufficient to see that an increase in the flow rate in zone 1 would make it possible to avoid the loss of paraxylene, by the raffinate. In the present case in less than one hour thirty paraxylene is entrained in zone 4. Just observation of the variation in the concentration profiles by means of the invention would make it possible to react quickly in relation to the good parameters.

Procedure No 4: The respective reference flow rates expressed at 150° C. are as follows:

| Solvent: 8.635 cm³/min | Zone 1: 42.735 cm³/min |
| Extract: 8.44 cm³/min | Zone 2: 34.295 cm³/min |
| Charge: 5.415 cm³/min | Zone 3: 39.71 cm³/min |
| Raffinate: 5.61 cm³/min | Zone 4: 34.10 cm³/min |

The losses represent about 0.5% of the total of the inputs. The compositions measured after 24 hours of steady-state operation of the unit are as follows:

| Extract | Raffinate |
|---|---|
| Toluene: 86.989% | Toluene: 23.950% |
| Ethylbenzene: 0.043% | Ethylbenzene: 10.705% |
| Paraxylene: 12.888% | Paraxylene: 2.355% |
| Metaxylene: 0.045% | Metaxylene: 49.008% |
| Orthoxylene: 0.015% | Orthoxylene: 13.992% |

Figure 7:
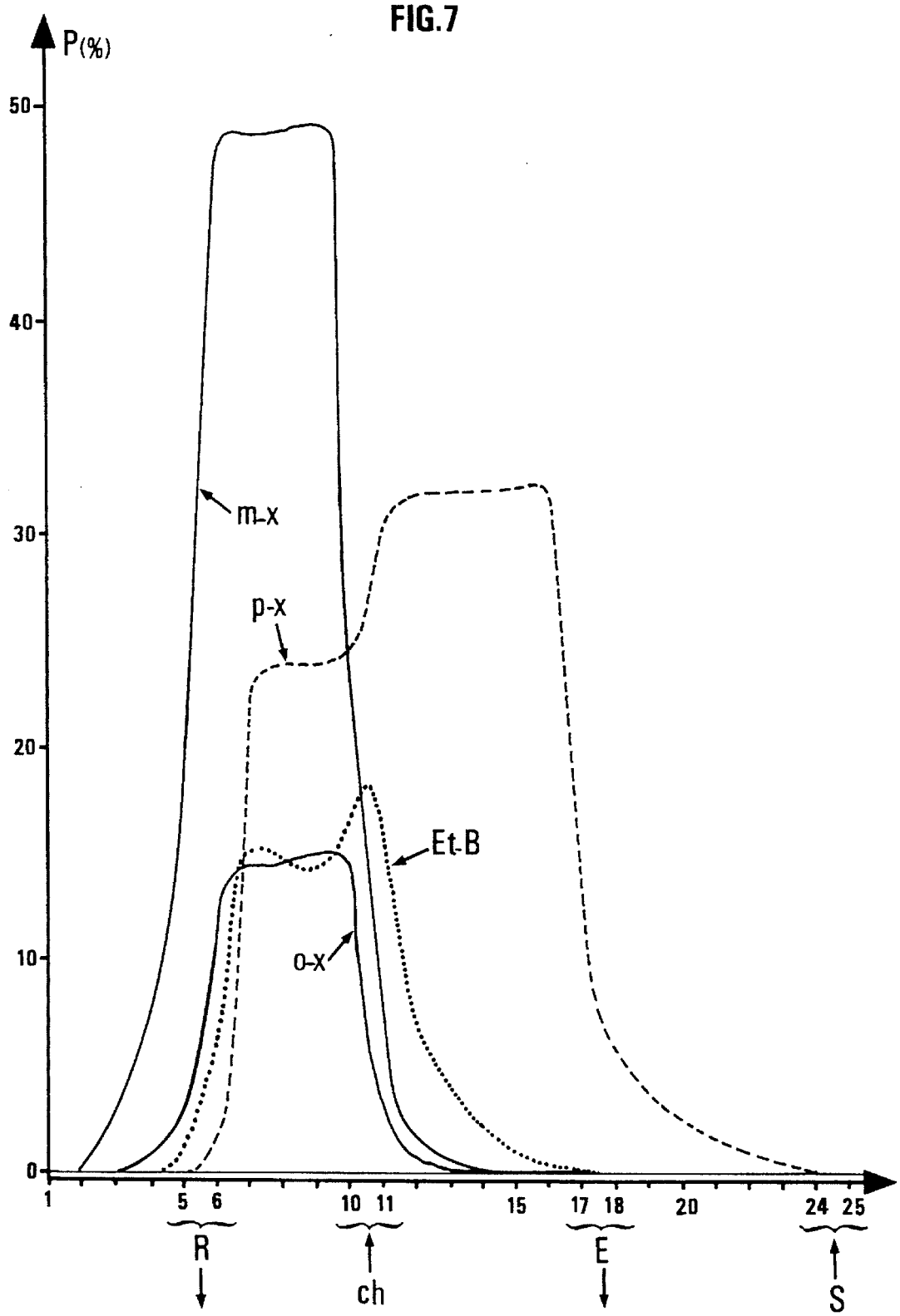

By means of the three sensors disposed in the internal circuit, a concentration profile is observed every 13 minutes and 20 seconds. In relation to procedure No 3 the profiles are considerably modified and during the transitional period-of operation the amount of ethylbenzene in the raffinate rises to 18% before stabilising at about 10.7%. Once again the ethylbenzene profile is completely modified while the paraxylene profile returns to a form which is fairly close to that of Example 2. In this procedure, paraxylene is obtained at a level of purity of higher than 99.2% just by means of modifying the recycle flow rate. While following the variation in the concentration profiles the reference values are not changed in spite of the variation in the composition of the raffinate which could seem alarming since those profiles are modified on approaching the desired profile: that shown in FIG. 7. Here the invention makes it possible to maintain the reference values in spite of a considerable variation in the composition of the effluents. In accordance with the prior art (just analysis of the effluents) the reference values would have been modified unwittingly.

EXAMPLE 4

A distilling column for producing orthoxylene at the bottom and a mixture of metaxylene, paraxylene and ethylbenzene at the head comprises two hundred and eighty real plates. The charge, depending on its composition, can be introduced at the 110th plate or the 135th plate. The reboiler is considered as the 282nd plate and the reflux balloon flask as the first.

The column is fed with two types of charge of the following compositions:

|  | Isomerisate | Tatoray unit effluent |
|---|---|---|
| EB | 10.2% | 4.0% |
| PX | 20.45% | 22.5% |
| MX | 48.10% | 50.1% |
| OX | 20.5% | 23.4% |
| Various impurities | 0.75% |  |

In order to respond to the hazards of a variable demand, the distilling column may be fed with either one of the two charges and possibly a mixture of the two. Regulation of that column is effected in accordance with the prior art by means of the following regulation effects: monitoring the charge flow rate, monitoring the reflux flow rate at the column head, monitoring the level of the reflux flask for drawing off distillate, monitoring the level in the reboiler for drawing off orthoxylene, monitoring the amount of combustion gas admitted into the oven by a temperature which can be sensed on the 225th plate. Daily monitoring of the composition of the distillate and the orthoxylene made it possible to ensure a level of purity of orthoxylene of 98.5% with a yield varying from 80 to 90%. That column is equipped with four optical sensors for providing for real-time analysis of the composition on the 280th, 255th, 120th and 2nd plates of the column. In addition a dynamic simulation model operates in accelerated time so as to calculate the responses of the column to the changes in compositions. The data relating to the real compositions are compared to the calculated compositions and the heating output of the reboiler, the reflux fete and the level of admission of the charge into the column are calculated in dependence on the compositions which are observed and calculated in real time. The mean level of purity of orthoxylene is thus changed from 98.5% to 98.9% while the yield fluctuates between 93 and 95%, that occurring without interruption or recycling during transient operating states, The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method of regulating a process for the separation of at least one isomer of aromatic hydrocarbon having from 8 to 10 carbon atoms which is contained in a mixture comprising at least two of said isomers, said process comprising a separation step in a separation zone, said method comprising:

a) sending a monochromatic light signal of a wavelength of between 400 and 1300 nanometers simultaneously to at least two points of said separation zone, other than points at which effluents are taken off, b) recovering a diffused polychromatic signal corresponding to the Raman effect between 400 and 3500 cm⁻, substantially at the level of said points of said separation zone of a), c) sending at least two recovered signals simultaneously to a multi-channel spectrometer and delivering the corresponding Raman spectra, d) determining the chemical composition of the mixture at each of the two points from the two spectra, e) repeating the sequence of steps a, b, c, and d so as to reconstitute profiles with respect to the concentration of the two isomers contained in the mixture, and f) comparing the profiles with respect to the concentration obtained to a predetermined reference concentration profiles and g) adjusting at least one operational variable of the separation process for regulating the process.

2. A method according to claim 1 wherein the separation process is a co-flow or counter-flow simulated mobile bed adsorption process.

3. A method according to claim 1 wherein the separation process is a process for the crystallisation in at least one crystallisation zone of a mixture comprising paraxylene, and wherein the chemical composition of the mixture is determined at at least two distinct points of said zone.

4. A method according to claim 1 wherein the separation process is a distillation process.

5. A method according to claim 1 wherein the chemical composition of the mixture is determined in a liquid phase.

6. A method according to claim 1 wherein the mixture is analysed at temperatures of between −70° and +220° C.

7. A method according to claim 1 wherein said monchromatic emission signal is also passed on to at least one of the effluents from the separation process, its chemical composition is determined and the composition of the effluent is compared to a predetermined reference composition.

8. A method according to claim 1 wherein the mixture to be separated comprises paraxylene, orthoxylene, metaxylene, ethylbenzene and toluene or paradiethylbenzene.

9. A method according to claim 1, wherein the wavelength of the monochromatic light signal is between 420 and 650 nanometers.

10. A method according to claim 1, wherein the Raman effect is between 600 and 1200 $cm^{-1}$.

11. A method according to claim 9, wherein the Raman effect is between 600 and 1200 $cm^{-1}$.

* * * * *